United States Patent [19]

Pless

[11] Patent Number: 5,163,428
[45] Date of Patent: Nov. 17, 1992

[54] IMPLANTABLE CARDIAC DEFIBRILLATOR WITH CURRENT LEAKAGE DETECTING MEANS

[75] Inventor: Benjamin D. Pless, Menlo Park, Calif.

[73] Assignee: Ventritex, Inc., Sunnyvale, Calif.

[21] Appl. No.: 597,204

[22] Filed: Oct. 11, 1990

[51] Int. Cl.⁵ ............................................. A61N 1/39
[52] U.S. Cl. .............................. 128/419 D; 128/908
[58] Field of Search ............ 128/419 D, 419 PT, 908, 128/419 PS

[56] References Cited

U.S. PATENT DOCUMENTS

| | | | |
|---|---|---|---|
| 3,886,932 | 6/1975 | Suessmilch | 128/908 |
| 4,080,558 | 3/1978 | Sullivan | 128/419 D |
| 4,088,141 | 5/1978 | Niemi | 128/908 |
| 4,102,347 | 7/1978 | Yukl | 128/908 |
| 4,164,946 | 8/1979 | Langer | 128/419 D |
| 4,165,749 | 8/1979 | Cansell | 128/419 D |
| 4,364,396 | 12/1982 | Barthel | 128/419 PT |
| 4,559,946 | 12/1985 | Mower | 128/419 D |
| 4,788,977 | 12/1988 | Farin et al. | 128/908 |
| 4,800,833 | 1/1989 | Winstrom | 128/419 D |
| 4,926,862 | 5/1990 | Miyajima et al. | 128/419 D |
| 5,111,816 | 5/1992 | Pless et al. | 128/419 D |

*Primary Examiner*—Kyle L. Howell
*Assistant Examiner*—Kennedy J. Schaetzle
*Attorney, Agent, or Firm*—Gerstman & Ellis

[57] ABSTRACT

An implantable cardiac deibrillator is provided having a battery, capacitive means, means coupled to the battery for charging the capacitive means, and means for coupling the capacitive means to a patient's heart, for delivering a high voltage shock to the heart. Current leakage from the capacitive means is detected. If the current leakage exceeds a predetermined amount, charging of the capacitive means is terminated. In one embodiment, voltage at the patient is directly sensed. In another embodiment, the voltage across a resistance located in series with the patient is sensed. In another embodiment, a test charge is provided for a short interval. The capacitive means is sensed to determine excessive loss of energy after the test charge. If excessive loss of energy is determined, charging is terminated.

17 Claims, 2 Drawing Sheets

IMPLANTABLE CARDIAC DEFIBRILLATOR WITH CURRENT LEAKAGE DETECTING MEANS

FIELD OF THE INVENTION

The present invention concerns a novel implantable cardiac defibrillator having a current leakage detecting means.

BACKGROUND OF THE INVENTION

It is believed that the first implantable defibrillator was implanted in a patient in 1980. Currently, thousands of individuals have devices implanted to correct cardiac conditions involving lethal tachyarrhythmias. It is anticipated that approximately 20,000 patients a year will receive these devices by the mid 1990's. As the use of the implantable defibrillator becomes more prevalent, insuring the safety of the device becomes more crucial.

A structure common to all implantable defibrillators is the high voltage output stage. Typically it is the interface between the high voltage energy storage capacitor (which is charged by a DC to DC converter) and the patient. An example of this is disclosed in U.S. Pat. No. 4,800,883.

A serious hazard to the patient exists if the electronic switches used in the output stage fail such that one or more becomes a comparatively low resistance. If this should occur, the output of the DC to DC converter is connected directly to the patient during high voltage capacitor charging. The resultant current flowing through the heart of the patient can initiate or accelerate an arrhythmia, cause direct tissue damage, or possibly result in death. While U.S. Pat. No. 4,164,946 refers to a fault detecting mechanism, this particular problem is not addressed. Furthermore, no currently available defibrillator incorporates an effective mechanism to guard against this hazard.

It is an object of this invention to provide a mechanism for preventing the high voltage charging circuit from being connected directly to the patient.

It is an additional object of this invention to provide the physician with a means to verify the integrity of the defibrillation output stage without delivering a shock to the patient.

Other objects and advantages of the invention will become apparent as the description proceeds.

SUMMARY OF THE INVENTION

In accordance with the present invention, an implantable cardiac defibrillator is provided. The defibrillator includes an energy source, energy storage means, and means coupled to the energy source for charging the energy storage means. Means are provided for coupling the energy storage means to a patient's heart, by delivering a high voltage shock to the heart. Means are provided for detecting current leakage from the energy storage means. Means responsive to the detecting means are provided for altering the charging of the energy storage means if the current leakage exceeds a predetermined amount.

In the illustrative embodiment, the altering means comprises means for terminating the charging.

In one embodiment, the detecting means comprises means for directly sensing voltage at the patient. In another embodiment, the detecting means comprises means for sensing the voltage across a resistance located in series with the patient.

In a further embodiment, means are provided for providing a test charge for a short interval. The detecting means comprises means for sensing the energy storage means to determine excessive loss of energy after the test charge. In this embodiment, the test charge providing means comprises means for providing an external command to perform the test charge for a period shorter than the natural refractory period of the heart.

In the illustrative embodiment, means are provided for synchronizing charging of the energy storage means to a sensed R-wave.

In an illustrative embodiment, the altering means comprises means for comparing a representation of the output from the detecting means to a reference voltage and for altering the charging of the energy storage means if the comparison indicates a fault. In an illustrative embodiment, the implantable cardiac defibrillator includes data storage means, and means responsive to the detecting means for storing current leakage information in the data storage means.

In accordance with a method of the present invention, a method is provided for operating an implantable cardiac defibrillator having an energy source, energy storage means, means coupled to the energy source for charging the energy storage means, and means for coupling the energy storage means to a patient's heart. The method includes the steps of detecting current leakage from the energy storage means and altering the charging of the energy storage means if the current leakage exceeds a predetermined amount.

In the illustrative embodiment, an external command is provided to provide a test charge to the energy storage means for a short interval. A first measurement of the voltage on the energy storage means is performed. At a predetermined time thereafter, a second measurement of the voltage on the energy storage means is performed. If the first voltage measurement exceeds the second voltage measurement by a predetermined amount, then the operation of the charging means is altered.

A more detailed explanation of the invention is provided in the following description and claims, and is illustrated in the accompanying drawings.

DETAILED DESCRIPTION OF THE ILLUSTRATIVE EMBODIMENTS

In an illustrative embodiment of the present invention, the defibrillator synchronizes charging to the timing of the heart by awaiting a sense event before beginning to charge. If there is a leakage from the output stage, synchronizing the beginning of the charge to the R-wave of the cardiac electrogram reduces the probability of causing or exacerbating an arrhythmia. Furthermore, the defibrillator output is monitored in one of a variety of ways to detect and report if leakage current to the patient is unacceptably high.

In one embodiment, the defibrillator output to the patient is monitored directly by a circuit which senses voltage. If the voltage at the patient due to current leakage exceeds some value, e.g. 500 millivolts, the charging episode is terminated. If the voltage at the patient remains below the threshold value, charging is allowed to continue normally. If the charging terminates due to a voltage detected at the patient due to current leakage, the information is stored for subsequent retrieval by the physician.

Alternatively, a resistor in series with the output stage and the patient may be monitored to directly measure the leakage current.

In another embodiment, a brief (approximately 100 msec, or some other period shorter than the natural refractory period of the heart), synchronized test charge is performed prior to the full capacitor charge. The voltage on the high voltage capacitors is measured immediately following the brief test charge. At some known interval following the first voltage measurement, a second voltage measurement is performed. The difference in voltages is indicative of the current escaping from the high voltage capacitors. If the second voltage measurement is unacceptably low, the charging episode is aborted on the likely assumption that leakage current to the patient is dangerously high. If the second voltage measurement is above the threshold value, then the charging is allowed to continue normally.

In addition to being performed automatically, a charging episode could also be routinely performed by the physician during regularly scheduled follow-up visits. If the output stage integrity is found to be compromised an immediate device replacement would be recommended.

Figure 1:
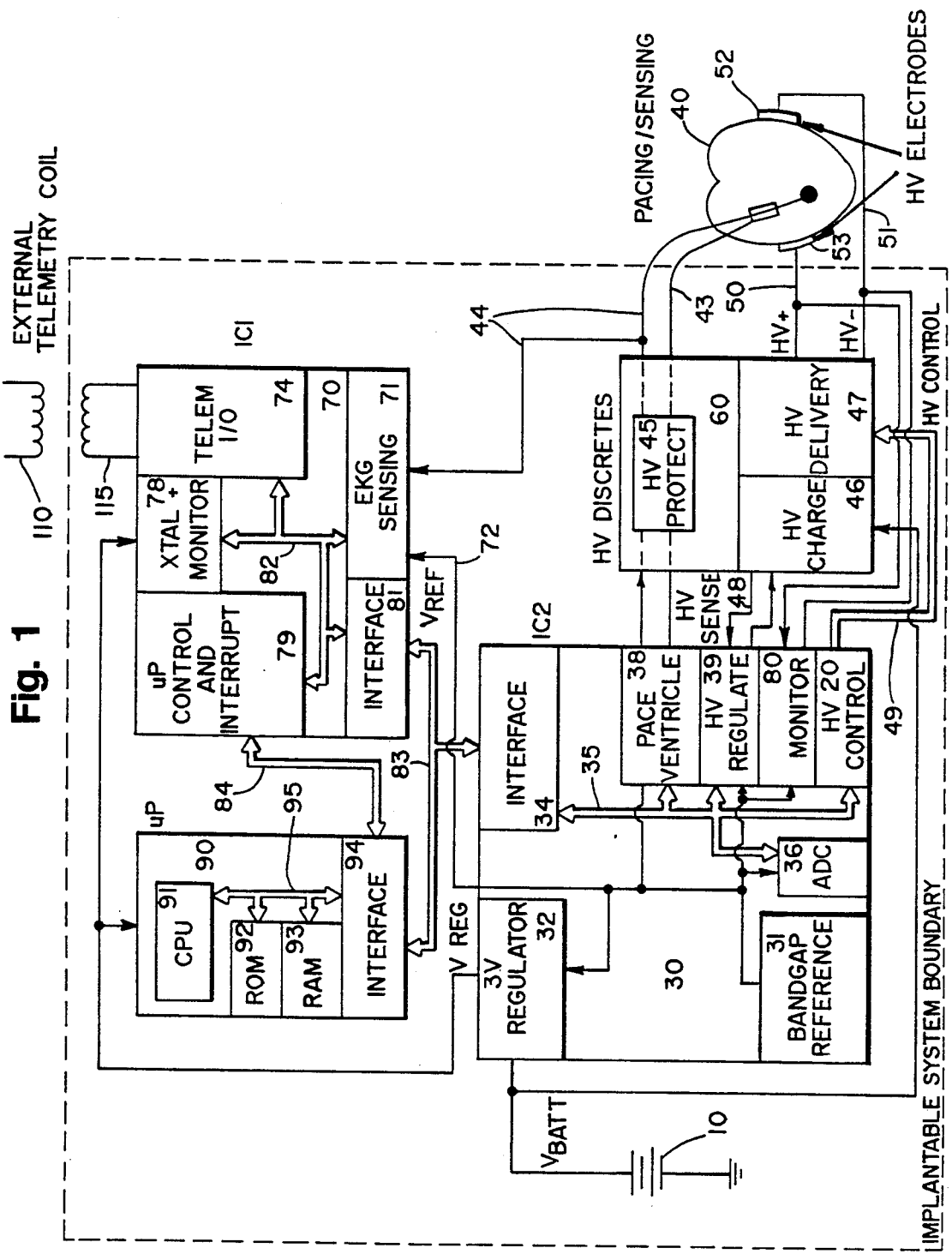
FIG. 1 is a block diagram of an implantable cardiac defibrillator constructed in accordance with the principles of the present invention.

The block diagram for the implantable defibrillator (shown in FIG. 1) includes integrated circuits and a set of high voltage discretes. The battery 10 produces a positive voltage with respect to ground that varies from about 6.4 volts when new, to 5.0 volts at the end of service. The battery directly powers IC2 30 and the high voltage discretes 60.

IC2 contains a band-gap reference circuit 31 that produces 1.235 volts, and a 3 volt regulator 32 that powers the microprocessor 90 and IC1 70 through line 100. The microprocessor 90 communicates with IC2 30 through a data and address bus 83 and an on-chip interface 34 that contains chip-select, address decoding and data bus logic as is typically used with microprocessor peripherals. The internal bus 35 allows the microprocessor to control a general purpose ADC 36, the ventricular pace circuits 38, and the HV control and regulate block 39. The ADC 36 is used to measure the battery, high voltage capacitor, and other voltages in the device.

The ventricular pace circuits 38 include a digital to analog converter that provides the ability to pace at regulated voltages. It communicates with the ventricle of a heart 40 through two lines. One line 43 is a switchable ground; the other line 44 is the pacing cathode and is also the input to the ventricular sense amplifier, as will be described below.

The ventricular pace lines pass through high voltage protection circuits 45 to keep the defibrillation voltages generated by the device from damaging the pacing circuits 38. The HV control and regulate block 39 on IC2 30 is used by the microprocessor 90 to charge a high voltage capacitor included in the HV charge block 46 to a regulated voltage, and then to deliver the defibrillating pulse to the heart 40 through the action of switches in the HV delivery block 47. An HV sense line 48 is used by the HV regulation circuits 39 to monitor the defibrillating voltage during charging. An HV control bus 49 is used by the HV control circuits 39 to control the switches in the HV delivery block 47 for delivering the defibrillating pulse to the electrodes 52, 53 through lines 50 and 51.

A monitor 80, which is the subject of this invention, receives inputs from the defibrillating output 50 and 51. The action of the monitor is described in detail below.

IC1 70 is also a microprocessor peripheral and provides timing, interrupt, telemetry, and sensing functions.

An electrogram sensing and waveform analysis section 71 interfaces with the ventricle of the heart 40 through line 44. The sensed electrogram is amplified and filtered. The amplifiers contained in this section 71 have multiple gain settings that are under microprocessor control for maintaining an automatic gain control. Features such as peak voltage and complex width are extracted by the waveform analysis circuits 71 for the microprocessor 90 to use in discriminating arrhythmias from normal sinus rhythm.

The crystal and monitor block 78 has a 100 KHz crystal oscillator that provides clocks to the entire system. The monitor is a conventional R-C oscillator that provides a back-up clock if the crystal should fail.

The microprocessor communicates with IC1 through two buses, 83 and 84. One bus 83 is a conventional data and address bus and goes to an on-chip interface 81 that contains chip select, address decoding and data bus drivers as are typically used with microprocessor peripherals. The other bus 84 is a control bus. It allows the microprocessor to set up a variety of maskable interrupts for events like timer timeouts, and sense events. If an interrupt is not masked, and the corresponding event occurs, an interrupt is sent from IC1 70 to the microprocessor 90 to alert it of the occurrence. On IC1 70, the up control and interrupt section 79 contains microprocessor controllable timers and interrupt logic.

The device can communicate with the outside world through a telemetry interface 74. A coil 115 is used in a conventional fashion to transmit and receive pulsed signals. The telemetry circuits 74 decode an incoming bit stream from an external coil 110 and hold the data for subsequent retrieval by the microprocessor 90. When used for transmitting, the circuit 74 receives data from the microprocessor 90, encodes it, and provides the timing to pulse the coil 115. The communication function is used to retrieve data from the implanted device, and to change the modality of operation if required.

The microprocessor 90 is of conventional architecture comprising a CPU 91, a ROM 92, a RAM 93, and interface circuits 94. The ROM 92 contains the program code that determines the operation of the device. The RAM 93 is used to modify the operating characteristics of the device as regards modality, pulse widths, pulse amplitudes, and so forth. Diagnostic data is also stored in the RAM for subsequent transmission to the outside world. The Central Processing Unit (ALU) 91 performs the logical operations directed by the program code in the ROM.

Figure 2:
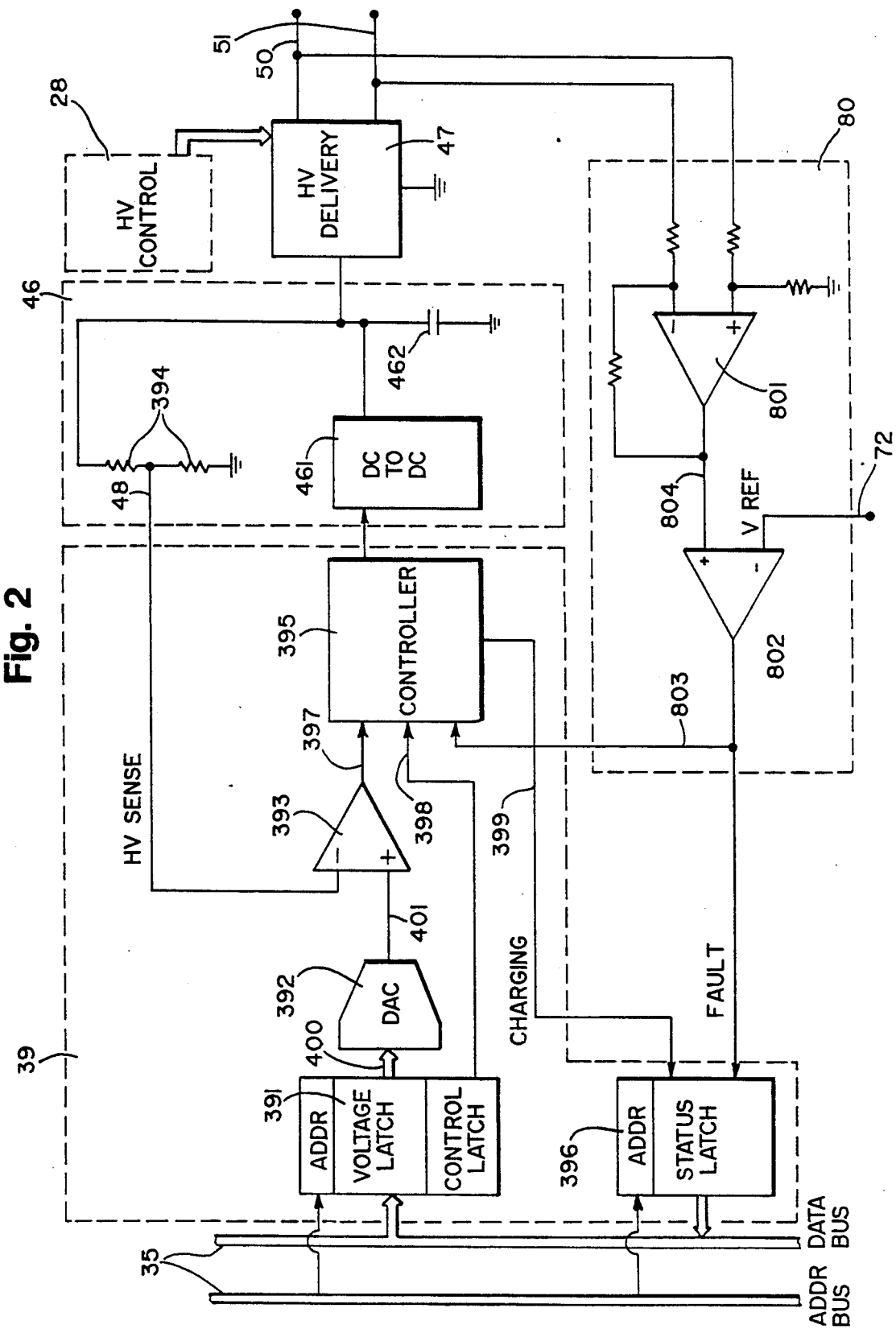
FIG. 2 is a schematic diagram of the monitor block and its association with the high voltage regulation block of the cardiac defibrillator of FIG. 1.

The monitor block 80 and its association with the HV regulate block 39 is shown in greater detail in FIG. 2. When the microprocessor initiates a charging sequence, it writes to latch 391. The address is decoded by the interface circuit 34 and strobes into the latch 391 the voltage and a command to start charging which is directed to the charging controller 395 through line 398. The charging episode may be commanded through the external coil 110, or may be automatic in response to a detected arrhythmia. However, in all events, in the preferred embodiment, the start of charging is synchronized to the heart.

The digital representation of the programmed voltage is sent along bus 400 to the DAC 392, which outputs an analog voltage to a comparator 393. As long as HV sense 48 is less than the voltage on line 401 the output of the comparator 397 remains high. The controller is designed to keep the DC-to-DC converter 461 turned on as long as the comparator output 397 remains high, the command from the microprocessor control latch on line 398 is high, and no fault is detected on line 803. Therefore, the DC-to-DC converter will keep charging the high voltage energy storage capacitor 462 until the desired voltage is reached as indicated by HV sense 48 exceeding the DAC output 397. HV sense 48 is related to the voltage on the capacitor 462 by the attenuation factor set by the resistor divider 394; this is typically a factor of 500. When the controller terminates charging, it outputs a signal on line 399 which is available in the status latch 396 for the microprocessor 90 to read.

In the absence of a failure in the HV delivery circuits 47, very little current leaks from the capacitor 462 through the leads 50 and 51 to the patient's heart 40. If current does leak to the patient, a voltage will be generated by the current flowing through the resistance of the patient's heart 40 and will be detected by the differential amplifier 801. If the output of the amplifier 804 exceeds the reference voltage 72 the comparator 802 output 803 will go high. Therefore, for a fixed reference voltage, the gain of the amplifier 801 sets the voltage value at the patient which is considered a fault. For the preferred embodiment, with a reference voltage of 1.235 volts, and a maximum desired voltage at the patient of 500 millivolts, the gain of the amplifier 801 is set at 2.47. Line 803 from the comparator goes to the status latch 396 and the controller 395. In the latter, the signal causes charging to terminate. In the former, it is latched into the status latch 396 for the microprocessor 90 to read.

In the preferred embodiment the voltage at the patient is directly monitored. However, as will occur to those skilled in the art, other methods of monitoring are also possible. Alternatively, the voltage across a resistor placed in series with the patient could be monitored; or the voltage on the high voltage capacitor after a synchronous test charge could be monitored to observe excessive capacitor droop which would be indicative of excessive current leakage to the patient.

Although illustrative embodiments of the invention have been shown and described, it is to be understood that various modifications and substitutions may be made by those skilled in the art without departing from the novel spirit and scope of the present invention.

What is claimed is:

1. An implantable cardiac defibrillator which comprises:
   an energy source;
   energy storage means;
   means coupled to said energy source for charging said energy storage means;
   means for coupling said energy storage means to a patient's heart, for delivering a high voltage shock to the heart;
   means for detecting current leakage to the patient from said energy storage means; and
   means responsive to said detecting means for altering the charging of said energy storage means if the current leakage exceeds a predetermined amount.

2. An implantable cardiac defibrillator as defined by claim 1, in which said altering means comprises means for terminating the charging.

3. An implantable cardiac defibrillator as defined by claim 1, said detecting means comprising means for directly sensing voltage at the patient.

4. An implantable cardiac defibrillator as defined by claim 1, further including a resistance located in series with the patient, said detecting means comprising means for sensing the voltage across said resistance.

5. An implantable cardiac defibrillator as defined by claim 1, including means for providing a test charge to said energy storage means for a short interval, said detecting means comprising means for sensing said energy storage means to determine excessive loss of energy after said test charge.

6. An implantable cardiac defibrillator as defined by claim 5, said test charge providing means comprising means for providing an external command to perform the test charge for a period shorter than the natural refractory period of the heart.

7. An implantable cardiac defibrillator as defined by claim 1, including means for synchronizing charging of said energy storage means to a sensed cardiac event.

8. An implantable cardiac defibrillator as defined by claim 7, in which said sensed cardiac event is a sensed R-wave.

9. An implantable cardiac defibrillator as defined by claim 1, said altering means comprising means for comparing a representation of the output from said detecting means to a reference voltage and for altering the charging of said energy storage means if the comparison indicates a fault.

10. An implantable cardiac defibrillator as defined by claim 1, in which said energy source is a battery and said energy storage means comprises capacitive means.

11. An implantable cardiac defibrillator as defined by claim 1, including data storage means and means responsive to said detecting means for storing current leakage information in said data storage means.

12. An implantable cardiac defibrillator which comprises:
    an energy source;
    energy storage means;
    means coupled to said energy source for charging said energy storage means;
    means for coupling said energy storage means to a patient's heart for delivering a high voltage shock to the heart;
    means for detecting current leakage to the patient from said energy storage means;
    means responsive to said detecting means for altering the charging of said energy storage means if the current leakage exceeds a predetermined amount;
    means for providing a test charge for a short interval, said detecting means comprising means for sensing said energy storage means to determine excessive loss of energy after said test charge;
    said test charge providing means comprising means for providing the test charge for a period shorter than the natural refractory period of the heart;
    means for synchronizing charging of said energy storage means to a sensed cardiac event; and
    means for reporting status.

13. An implantable cardiac defibrillator which comprises:

a battery;

capacitive means;

means coupled to said battery for charging said capacitive means;

means for coupling said capacitive means to a patient's heart for delivering a high voltage shock to the heart;

means for synchronizing charging of said capacitive means to a sensed R-wave;

means for detecting current leakage to the patient from said capacitive means;

means responsive to said detecting means for altering the charging of said capacitive means if the current leakage exceeds a predetermined amount;

said altering means comprising means for comparing a representation of the output from said detecting means to a reference voltage and for altering the charging of said capacitive means if the comparison indicates a fault.

14. A method for operating an implantable cardiac defibrillator having an energy source, energy storage means, means coupled to said energy source for charging said energy storage means, and means for coupling said energy storage means to a patient's heart, including the steps of:

detecting current leakage to the patient from said energy storage means; and altering the charging of said energy storage means if the current leakage exceeds a predetermined amount.

15. A method as defined by claim 14, said altering steps comprising the step of terminating charging of said energy storage means if the current leakage exceeds a predetermined amount.

16. A method for operating an implantable cardiac defibrillator having an energy source, energy storage means, means coupled to said energy source for charging said energy storage means, means for coupling said energy storage means to a patient's heart, including the steps of:

providing an external command to provide a test charge to said energy storage means for a short interval;

performing a first measurement of the voltage on the energy storage means;

at a predetermined time thereafter, performing a second measurement of the voltage on the energy storage means;

if the first voltage measurement exceeds the second voltage measurement by a predetermined amount, then altering the operation of said charging means.

17. A method as defined by claim 16, said altering step comprising the step of terminating the operation of said charging means.

* * * * *